United States Patent [19]
Vanney et al.

[11] Patent Number: 6,076,529
[45] Date of Patent: Jun. 20, 2000

[54] TRANSMYOCARDIAL IMPLANT WITH INSERTED VESSEL

[75] Inventors: Guy P. Vanney, Blaine; Katherine S. Tweden, Mahtomedi, both of Minn.

[73] Assignee: Heartstent Corporation, St. Paul, Minn.

[21] Appl. No.: 09/063,161

[22] Filed: Apr. 20, 1998

[51] Int. Cl.$^7$ .................................................. A61B 19/00
[52] U.S. Cl. ............................ 128/898; 623/1.15; 604/8; 606/194
[58] Field of Search ................. 623/1, 3, 11, 12, 623/66, 1.15; 128/897, 898; 604/8; 606/194

[56] References Cited

U.S. PATENT DOCUMENTS

| | | |
|---|---|---|
| 5,409,019 | 4/1995 | Wilk . |
| 5,655,548 | 8/1997 | Nelson et al. . |
| 5,755,682 | 5/1998 | Knudson et al. ............................ 604/8 |
| 5,807,384 | 9/1998 | Mueller ....................................... 604/7 |
| 5,810,836 | 9/1998 | Hussein et al. .......................... 606/108 |

OTHER PUBLICATIONS

Goldman, A. et al., "Experimental Methods for Producing a Collateral Circulation to the Heart Directly From the Left Ventricle", *J. Thoracic Surg.*, 31(3):364–374 (Mar. 1956).

Massimo, C. et al., "Myocardial Revascularization by a New Method of Carrying Blood Directly From the Left Ventricular Cavity into the Coronary Circulation", *J. Thoracic Surg.*, 34(2):257–264 (Aug. 1957).

Munro, I. et al., "The possibility of myocardial revascularization by creation of a left ventriculocoronary artery fistula", *Thoracic and Cardiovascular Surgery*, 58(1):25–32 (Jul. 1969).

*Primary Examiner*—Dinh X. Nguyen
*Attorney, Agent, or Firm*—Merchant & Gould P.C.

[57] ABSTRACT

A transmyocardial implant includes a hollow conduit inserted through a heart wall. The conduit defines a blood flow path between a heart chamber opening and a vessel opening. The heart chamber opening of the conduit is placed in communication with a chamber of the heart. A coronary vessel on an exterior of the heart wall is severed into a proximal portion and a distal portion. The distal portion of the vessel is placed into the vessel opening of the conduit. An alternative embodiment places the vessel flush with the vessel opening of the conduit.

6 Claims, 2 Drawing Sheets

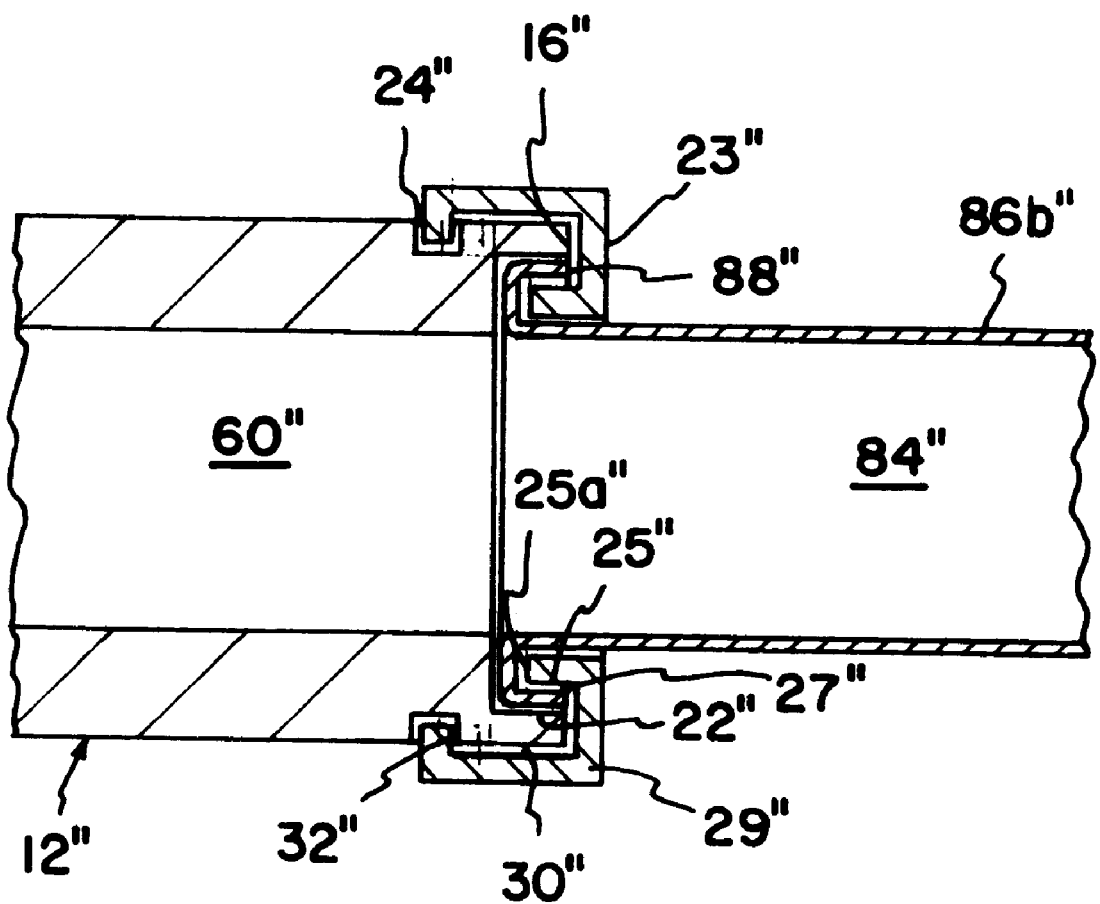

6,076,529

TRANSMYOCARDIAL IMPLANT WITH INSERTED VESSEL

BACKGROUND OF THE INVENTION

1. Field of the Invention

This invention pertains to an implant for passing blood flow directly between a chamber of the heart and a coronary vessel. More particularly, this invention pertains to a transmyocardial implant with a coronary vessel inserted into the implant.

2. Description of the Prior Art

Commonly assigned and co-pending U.S. patent application Ser. No. 08/882,397 having related PCT Application No. PCT/US97/13980, entitled "Method and Apparatus for Performing Coronary Bypass Surgery", and filed on Jun. 25, 1997 in the name of inventors Mark B. Knudson and William L. Giese, teaches an implant for defining a blood flow conduit directly from a chamber of the heart to a lumen of a coronary vessel. An embodiment disclosed in the aforementioned application teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 09/009,400 filed Jan. 20, 1998, entitled "Flexible Transmyocardial Implant", and filed in the name of inventor Katherine S. Tweden teaches a transmyocardial implant. The implant includes a rigid conduit placed in the myocardium and which has a vessel graft extending from the conduit to a coronary vessel.

Implants such as those shown in the aforementioned '397 application include a portion to be placed within a coronary vessel and a portion to be placed within the myocardium. When placing the implant in a coronary vessel such as a coronary artery, the vessel may be stretched to fit over the implant. Too much stretching of the artery may result in arterial damage. The risk of excessive stretching is most likely when placing an implant into a small diameter vessel (e.g., 1–2 mm). As the diameter of the implant decreases to accommodate smaller vessels, the ratio of the wall thickness of the implant to the diameter increases. Therefore, the proportional amount of stretching increases with smaller implants. The amount of stretching can be reduced by decreasing the wall thickness of the implant.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart. A hollow conduit is inserted through the heart wall. The conduit defines a blood flow path between a heart chamber opening and a vessel opening. The heart chamber opening of the conduit is placed in communication with a chamber of the heart. The vessel is severed into a proximal portion and a distal portion. The distal portion of the vessel is placed into the vessel opening of the conduit. An alternative embodiment places the vessel flush with the vessel opening of the conduit.

BRIEF DESCRIPTION OF THE DRAWINGS

FIG. 6 is an enlarged cross-sectional view of the vessel opening of the conduit of FIG. 2 showing an alternative embodiment for attaching the vessel to the conduit in a manner resulting in the interior of the conduit being substantially flush with the lumen of the vessel.

DESCRIPTION OF THE PREFERRED EMBODIMENT

Figure 1:
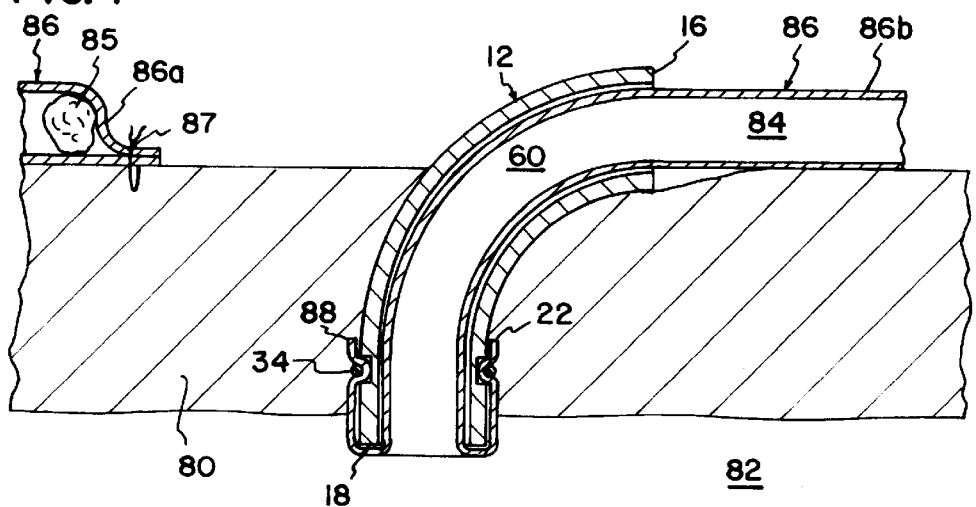
FIG. 1 is a cross-sectional view of one embodiment of the present invention showing a conduit placed in a heart wall and showing a distal portion of a coronary vessel extending through the length of the conduit.

Referring now to the various drawing figures, a description of a preferred embodiment will now be provided. Three embodiments are illustrated in the drawings. Similar elements are numbered similarly with apostrophes and double apostrophes employed to distinguish embodiments.

With initial reference to FIG. 1, an implant is shown including a hollow, rigid conduit 12. The conduit 12 may be formed of titanium or other rigid biocompatible material such as pyrolytic carbon or may be titanium coated with pyrolytic carbon. The material of the conduit 12 is preferably a rigid material in order to withstand contraction forces of the myocardium 80. While the conduit 12 is described as a solid, rigid cylinder, the conduit 12 can be any structure (e.g., an expanded stent) suitable to hold open a path through the myocardium 80 during both systole and diastole.

The conduit 12 is sized to extend through the myocardium 80 of the human heart to project into the interior of a heart chamber 82 (preferably, the left ventricle) by a distance of about 5 mm. By way of non-limiting example, the conduit 12 will have an outside diameter of about 3 millimeters and an internal diameter of about 2 millimeters to provide a measured as the distance between the inner and outer surface of the conduit of about 0.5 millimeters. The conduit 12 extends from a first end (or vessel opening) 16 to a second end (or heart chamber opening) 18. adjacent to the second end 18, the exterior wall of the conduit 12 is provided with a circumferential groove 22, the purpose of which will be described.

Although not shown for ease of illustration, the outer surface of the conduit 12 may be provided with tissue-growth inducing material to further immobilize the conduit 12 within the myocardium 80. Such a material on a transmyocardial implant is discussed more fully in commonly assigned and co-pending U.S. patent application Ser. No. 08/944,313.

By way of non-limiting example, the conduit 12 is shown in use for bypassing an occlusion 85 in a coronary artery 86. The coronary artery 86 is severed distal to the occlusion 85. The severance divides the artery 86 into a proximal portion 86a and a distal portion 86b. The proximal portion 86a is ligated distal to the obstruction 85 by sutures 87.

The distal portion 86b is dissected from the myocardium 80. A free end 88 of the distal portion 86b of the artery 86 is inserted into the vessel opening 16 of the conduit 12. The free end 88 is passed completely through the interior of the conduit 12 and folded over the heart chamber end 18 of the conduit 12. The free end 88 of the distal artery portion 86b partially covers the exterior of the conduit 12 adjacent the second end 18 of the conduit 12 and covers the groove 22. The free end 88 is secured to the conduit 12 by sutures 34 tightly placed around the exterior of the distal artery portion 86b overlying the groove 22.

The conduit 12 and attached distal artery portion 86b are placed in the myocardium 80 with the second end 18 protruding into the left ventricle 82. The conduit 12 and attached distal artery portion 86b thus define an open blood flow path 60 having a first end in blood flow communication with the left ventricle 82. The blood flow path 60 communicates directly with the lumen 84 of the coronary artery 86 lying on an exterior of the heart wall 80.

With the above-described embodiment, the implant permits revascularization from the left ventricle 82 to a coronary vessel such as a coronary artery 86 (or a coronary vein in the event of a retrograde profusion procedure). The use of distal artery portion 86b as described results in blood flowing through path 60 being exposed only to natural biological material thereby reducing risk of thrombosis. As shown in FIG. 1, the free end 88 of the distal portion 86b of the artery 86 is wrapped around the conduit 12 so that no portion of the conduit 12 is in contact with blood within the left ventricle 82. Therefore, a broader range of materials and structures can be used for the conduit 12 since there is no direct blood contact with the conduit 12.

Since the conduit 12 may have a length of about 25 mm, a similar length of the distal portion 86b of the artery 86 must be dissected from the myocardium 80. In dissecting the artery 86, septal perfusing or branching arteries (not shown) should be ligated. The ligation of septal perfusing or branching arteries results in deprivation of blood flow to a portion of the myocardium 80 nourished by the ligated arteries. As an alternative, the vessel to be inserted into the conduit 12 may be a coronary vein instead of a coronary artery as described. If a vein is used, the vein is ligated and a portion of the vein otherwise draining the myocardium is placed in the conduit 12. Blood then flows in a direction reverse to normal flow (i.e., the myocardium is nourished by the vein). A vein may be advantages for numerous reasons. For example, a vein is less susceptible to stenosis and can usually be sacrificed without risk to a patient. Further, use of a vein means septal perforators need not be sacrificed. If a vein is used, a corresponding artery may need to be occluded and redirected to the right ventricle to drain blood from the myocardium.

Figure 2:
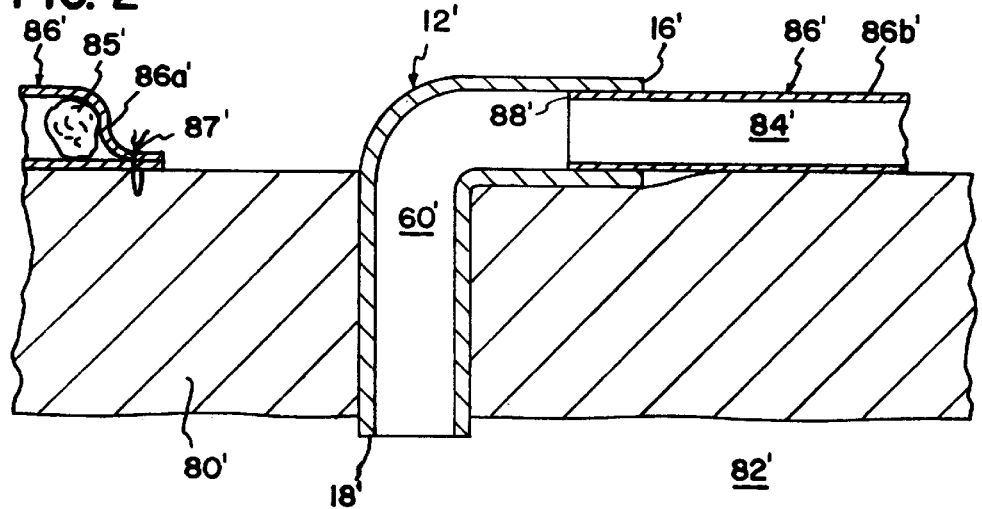
FIG. 2 is a cross-sectional view of a second embodiment of the present invention showing a conduit placed in a heart wall and showing a distal portion of a coronary vessel positioned within the conduit adjacent a vessel opening of the conduit.

In the event the embodiment of FIG. 1 results in excessive ligation of septal perfusing or branching arteries, the embodiment of FIGS. 2–5 inserts the artery 86' within the conduit 12' but requires only a short dissected length of the artery 86'. In FIG. 2, the free end 88' of the artery distal portion 86b' is inserted into the vessel opening 16' of the conduit 12'. The free end 88' is secured to the conduit 12' adjacent the vessel opening 16'. In this embodiment, blood flow is in contact with the conduit material. A thrombus resistant material is preferred. Such materials for the conduit 12' include titanium as well as titanium coated with an anti-thrombotic coating.

Figure 3:
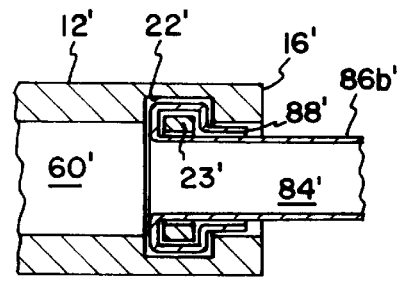
FIG. 3 is an enlarged cross-sectional view of the vessel opening of the conduit of FIG. 2 showing one embodiment for attaching the vessel to the conduit.
Figure 4:
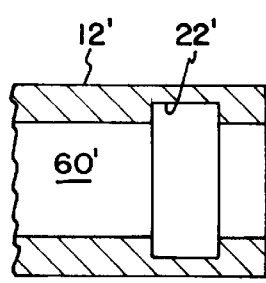
FIG. 4 is a cross-sectional view showing the vessel portion of the conduit of FIG. 3 without an attached vessel.
Figure 5:
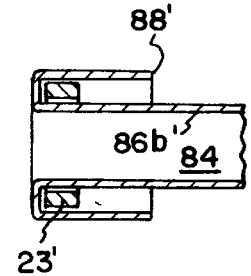
FIG. 5 is a cross-sectional view showing the distal portion of the vessel of FIG. 3 with an attachment ring in place before connection to the conduit of FIG. 4.

FIGS. 3–5 illustrate a specific structure for attaching the free end 88' of the vessel distal portion 86b' to the interior of the conduit 12'. The interior wall of the conduit 12' is provided with an annular groove 22' adjacent the conduit's vessel opening 16'. A snap ring 23' is provided having a size selected to fit into the groove 22'. The snap ring 23' is deformable to be compressed to pass from the exterior of the conduit 12' and through the vessel opening 16' to the groove 22'. At the groove 22', the ring 23' is biased into and retained within the groove 22'.

To assemble the connection, the free end 88' of the artery distal portion 86b' is inserted through the ring 23' and folded back over the exterior of the ring 23' (FIG. 5). The ring 23' and free end 88' are inserted into the vessel opening 16' of the conduit 12' until the ring 23' is received within the groove 22' thereby holding the free end 88' within the conduit 12'.

FIG. 6 illustrates an alternative embodiment to FIG. 3 where the free end 88" is attached to the conduit 12" in a manner such that the lumen 84" of the artery distal portion 86b" is substantially flush with the interior wall of the conduit 12".

At the vessel opening 16", the conduit 12" is provided with an annular groove 22" on the interior of the conduit 12" at the opening 16". An outer annular groove 24" is formed in the exterior wall of the conduit 12" spaced from the vessel opening 16". A coupling 23" secures the free end 88" of the artery distal portion 86b" to the conduit 12".

The coupling 23" is a ring symmetric about a cylindrical axis. The ring 23" has an inner cylindrical portion 25" sized to be received within the inner groove 22". Opposing cylindrical surfaces of the inner cylindrical portion 25" and the conduit 12" define an annular space 27" sized to receive a thickness of the vessel free end 88".

The ring 23" has a radial wall 29". The wall 29" abuts the end 16" of the conduit 12" when a radial end 25a" of the inner cylindrical portion 25" is spaced from an opposing surface of the conduit 12" by a spacing slightly less than the thickness of the vessel distal portion 86b".

The ring 23" includes a snap ring 30" having a snap lock 32". The snap lock 32" is positioned to be received within the outer groove 24" when the radial wall 25a" abuts the end 16" of the conduit 12".

With the ring 23" disconnected from the conduit 12", the free end 88" of the vessel distal portion 86b" is looped over the inner cylindrical portion 25". The ring 23" is snapped onto the conduit 12". The vessel 86b" is compressed between the conduit 12" and the radial end 25a" and within the annular space 27". So positioned, the free end 88" is secured to the conduit 12" with the lumen 84" flush with the interior wall of the conduit 12".

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto.

What is claimed is:

1. A method for performing a coronary bypass procedure at a coronary vessel disposed lying at an exterior of a heart wall, the method comprising:

inserting a hollow conduit through the heart wall where the conduit has an interior wall defining a blood flow path between a heart chamber opening and a vessel opening, said inserting including placing the heart chamber opening of the conduit in communication with a chamber of the heart;

severing the vessel into a proximal portion and a distal portion and dissecting free a length of the distal portion sufficient to insert the dissected length into the conduit;

inserting the dissected length of the distal portion of the vessel into the vessel opening of the conduit with an exterior of the dissected length opposing the interior wall of the conduit; and securing the dissected length of the distal portion of the vessel to the conduit.

2. A method according to claim 1 wherein the vessel is a coronary artery and the heart chamber is a left ventricle, said method further comprising severing the artery distal to an obstruction in the artery.

3. A method according to claim 1 wherein the dissected length of the distal portion of the coronary vessel is inserted into a full length of the conduit to the heart chamber opening.

4. A method according to claim 3 wherein the dissected length of the distal portion of the coronary vessel is wrapped around an exterior of the conduit at the heart chamber opening.

5. A method according to claim 1 wherein the dissected length of the distal portion of the coronary vessel is inserted into the conduit at the vessel opening and secured to the conduit adjacent the vessel opening.

6. A method for performing a coronary bypass procedure at a coronary vessel disposed lying at an exterior of a heart wall, the method comprising:

inserting a hollow conduit through the heart wall where the conduit has an interior surface defining a blood flow path between a heart chamber opening and a vessel opening, said inserting including placing the heart chamber opening of the conduit in communication with a chamber of the heart;

severing the vessel into a proximal portion and a distal portion;

attaching the distal portion of the vessel to the conduit at the vessel opening of the conduit with an interior surface of the distal portion of the vessel substantially flush and continuous with the interior surface of the conduit to define a substantially continuous, uniform diameter transition between said blood flow path and a lumen of said vessel.

* * * * *

UNITED STATES PATENT AND TRADEMARK OFFICE
CERTIFICATE OF CORRECTION

PATENT NO.   : 6,076,529
DATED        : June 20, 2000
INVENTOR(S)  : Vanney et al.

It is certified that error appears in the above-identified patent and that said Letters Patent is hereby corrected as shown below:

<u>Title page,</u>
Item [56], References Cited, insert the following before OTHER PUBLICATIONS,

-- FOREIGN PATENT DOCUMENTS
WO 98/08456         3/1998         WIPO --

Signed and Sealed this

Twenty-sixth Day of August, 2003

JAMES E. ROGAN
*Director of the United States Patent and Trademark Office*